US009764050B1

(12) United States Patent
Almeida et al.

(10) Patent No.: US 9,764,050 B1
(45) Date of Patent: Sep. 19, 2017

(54) SANITIZING MAT

(71) Applicants: Stephen Almeida, St. Petersburg, FL (US); James Kerr, Scarborough, ME (US); Sonya Messer, Falmouth, ME (US)

(72) Inventors: Stephen Almeida, St. Petersburg, FL (US); James Kerr, Scarborough, ME (US); Sonya Messer, Falmouth, ME (US)

(73) Assignee: SANITIZALL, LLC, Scarborough, ME (US)

( * ) Notice: Subject to any disclaimer, the term of this patent is extended or adjusted under 35 U.S.C. 154(b) by 0 days.

(21) Appl. No.: 15/346,146

(22) Filed: Nov. 8, 2016

(51) Int. Cl.
*A61L 2/10* (2006.01)
*A47L 23/22* (2006.01)
*A61L 2/24* (2006.01)

(52) U.S. Cl.
CPC ...... *A61L 2/10* (2013.01); *A61L 2/24* (2013.01); *A61L 2202/14* (2013.01)

(58) Field of Classification Search
CPC .......... A61L 2/10; A61L 2/0047; A47L 23/22; A47L 23/266
USPC ...... 422/24, 22, 186; 250/504 R, 492.1, 431, 250/454.11; 15/215
See application file for complete search history.

(56) References Cited

U.S. PATENT DOCUMENTS

| 6,886,210 | B2 * | 5/2005 | Dean ...... A47L 23/266 15/104.92 |
| 8,470,239 | B1 * | 6/2013 | Kerr ...... A61L 2/10 422/22 |
| 8,631,533 | B1 * | 1/2014 | Gulian ...... A61L 2/10 15/36 |
| 9,198,991 | B2 * | 12/2015 | Dombrowsky ...... A61L 2/10 |
| 9,211,352 | B2 * | 12/2015 | Kassel ...... A61L 2/10 |
| 9,579,410 | B2 * | 2/2017 | Simmons ...... A61L 2/10 |
| 2010/0104470 | A1 * | 4/2010 | McCabe ...... A61L 2/10 422/22 |
| 2012/0187313 | A1 * | 7/2012 | Clark ...... A61L 2/10 250/492.1 |
| 2013/0154441 | A1 * | 6/2013 | Redmond ...... G08G 1/02 310/319 |
| 2013/0177474 | A1 * | 7/2013 | Kerr ...... A61L 2/0047 422/24 |
| 2013/0259742 | A1 * | 10/2013 | Kerr ...... A61L 2/10 422/24 |
| 2015/0308091 | A1 * | 10/2015 | Foust ...... E03D 13/00 4/309 |

(Continued)

*Primary Examiner* — David A Vanore
(74) *Attorney, Agent, or Firm* — JEDA Technologies; James G. Shelnut

(57) ABSTRACT

The present invention relates to sanitization devices and methods. More particularly, the invention relates to devices and methods that significantly reduce or eliminate germs, bacteria and/or other microorganisms from objects such as bags, purses, footwear or other objects, as well as bare feet, hands, paws, hooves or other anatomical surfaces, which come into contact with them. The device and method uses germicidal radiation which exposes only the areas of the object that come into applied contact with the device. The device contains an array of individual cells which are configured to turn on and off sanitizing radiation. The devices may be interconnected to fill a large area such as a lobby, the floor of a hospital and the like.

15 Claims, 5 Drawing Sheets

(56) References Cited

U.S. PATENT DOCUMENTS

2016/0175896 A1\* 6/2016 Montgomery ........ B08B 7/0057
250/454.11

\* cited by examiner

SANITIZING MAT

FIELD OF DISCLOSURE

The present disclosure relates to sanitization devices and methods. More particularly, the disclosure relates to sanitizing mats and methods that significantly reduce or eliminate germs, bacteria and/or other pathogenic microorganisms from objects such as bags, purses, footwear or other objects, as well as bare feet, hands, paws, hooves or other anatomical surfaces, which come into contact with them. The device and method uses germicidal radiation which exposes only the areas of the object that come into contact with the device. The mats may be interconnected so that a significantly large area can be covered with sanitizing devices.

BACKGROUND OF THE DISCLOSURE

Bacteria, viruses, germs, molds, fungi and other undesirable, pathogenic microorganisms are transferred from one area to another through contact with people, animals and objects that come into contact with them.

The present disclosure is concerned with the problem of spreading microorganisms that are carried on the outer surfaces of footwear and other objects as well as hands, feet, paws, hooves and other anatomical surfaces that have been exposed to areas contaminated with undesirable microorganisms. The outer bottom surfaces of footwear such as soles and heels can come into contact with floor areas or outdoor ground areas that may be unsanitary and contaminated with microorganisms such as bacteria, viruses, germs molds, and fungi. Areas where such microbial contamination commonly exists include hospital areas, such as emergency rooms, food handling areas such as food markets, restaurants, schools, recycling areas, and refuse dumps as well as public toilets, public sidewalks and streets, handrails on staircases and escalators, parks, park benches, farms, or anywhere that the public frequents. In some situations, undesirable microorganisms can be picked up from something as simple and ubiquitous as a backyard.

Someone or something that has been contaminated with an undesirable microorganism can easily and unknowingly spread the microorganisms around. In some cases, the contamination can result from urine in areas near public toilets and urinals, animal urine and feces as well as human sputum on sidewalks, streets, lawns, etc. as well as other bodily fluids.

The outer surfaces of other objects such as suitcases, handbags, purses, briefcases, packages, and the like which come into contact with such contaminated areas as airport bathrooms, bars, schools, hospitals and restaurants which may expose them to domestic and international microorganisms also become contaminated and thereby become a source of further microbial contamination and spreading. Thus, footwear and other objects can carry microorganisms into the home, office, car or other personal areas and to those most susceptible to microorganism such as young children and older people.

Further, house pets that have come into contact with contaminated areas such as parks, yards, and the like can also carry undesirable microorganisms into the home. In livestock areas cattle, horses, sheep and the like constantly come into contact with undesirable microorganisms and spread them around on the paws, hooves or feet.

In all these scenarios, a person's hands may also become contaminated by touching a contaminated area. This will result in the transfer of the pathogenic microorganisms into the body through subsequent touching of the mouth, eyes, ears, and such. Similarly, bare feet can be exposed to microorganism contamination when walking bare foot outside or in locker rooms, pools, showers and the like and further spread them.

It is therefore highly desirable to eliminate or significantly reduce the amounts of these microorganisms from surfaces that carry them.

Solutions to this problem have been disclosed whereby devices containing fluid disinfectants either wet the bottom of footwear through sponge applications or a disinfectant is sprayed onto the bottom of footwear. The solutions create other problems such as slippery soles, tracking of the fluids and potential exposure to toxic materials relating to the disinfectant. A dry method would thus be more desirable.

A device described in US Pat. Appl. 2010/0193709 utilizes a platform that is transparent to UVC sanitizing radiation used to disinfect a shoe or foot. The transparent platform is made of glass which blocks a certain portion of the UV light with only a remainder of the light illuminating the shoe or foot. The platform may also be a metal grid allowing for the UVC light to shine through. The application also describes a cover that the feet or shoes go into so that any stray UVC light does not escape. The glass used in this application blocks the disinfecting UVC wavelength of 254 nm and allows through the non-disinfecting UVB and UVA wavelengths and is therefore not suitable for disinfecting applications. The cover in this application presents a tripping hazard as well as an imperfect cover for blocking stray UVC light.

A device described in US Pat Appl. 2010/0104470 describes a device that uses a UV light along with a platform preferably made of Plexiglas and a "soft plastic material" on top of the platform with a gel between the plastic and the Plexiglas that is absorptive of the UV light. When a shoe steps on the platform the gel will be pushed aside and the UV will shine through the Plexiglas, the "soft plastic material" and onto the sole of the shoe. Radiation with germicidal activity is 254 nm which will not pass through Plexiglas which is polymethylmethacrylate. Although the application states other transparent materials can be used for the platform, no enabling materials are described therefore leaving those skilled in the art to perform a substantial amount of research to find suitable materials. Additionally, the application states "soft plastic materials" that are substantially transparent to the disinfecting radiation can be used, without any suggestion as to what those materials might be, again leaving it to the practitioner to perform a substantial amount of research to determine a material which is soft, pliable and transparent to the disinfecting radiation, which again is 254 nm. While many gels absorb radiation there, not any gel will be suitable for this application. The gel needs to have to correct viscosity so that it will push away when pressure is applied but not be so viscous that when pressure is removed, the gel will flow back into the area creating a substantially uniform thickness ready for the next shoe to disinfect.

Thus, more efficient devices and methods and more suitable materials are needed to properly eliminate or significantly reduce undesirable microorganisms. Additionally, these are no provisions for hands sanitation, house pet sanitation or other animal sanitation.

SUMMARY OF THE EXEMPLARY EMBODIMENTS

It is an object of the current invention to overcome the deficiencies commonly associated with the prior art as discussed above and provide devices and methods that eliminate or significantly reduce undesirable and/or pathogenic microorganisms from objects such as, for example, bags, purses, footwear or other objects, bare feet, hands, paws, hooves or other anatomical surfaces.

In a first embodiment, a sanitizing apparatus is provided for the elimination or significant reduction of undesirable or pathogenic microorganisms from objects which contains a housing having a housing having a top, a bottom and sides, wherein the volume of the housing is segmented into an array of individual, interconnected, geometrically shaped cells, each cell having sides that define the cell. The sides of the cells are made of structural material and are positioned orthogonal to the bottom of the housing and extend from the bottom of the housing fully or partially to the top of the housing, each cell having at least one of a sanitizing radiation emitter, an infrared radiation sensor, and a visible radiation sensor, positioned in the area of the bottom of the cell.

In a second embodiment, a sanitizing apparatus of the above embodiment is provided wherein the housing top comprises a structural layer positioned covering the top of the cells, wherein the layer allows at least a portion of the sanitizing radiation to pass through.

In a third embodiment, a sanitizing apparatus of each of the above embodiments is provided wherein the infrared radiation sensor is electronically coupled to the sanitizing radiation emitter, and wherein the radiation emitter is capable of being activated when the infrared sensor senses no infrared radiation.

In a fourth embodiment, a sanitizing apparatus of each of the above embodiments is provided further having electrical connectors wherein the electrical connectors are configured to allow at least two apparatuses to be electrically connected.

In a fifth embodiment, a sanitizing apparatus of each of the above embodiments is provided further having a low frequency transducer, wherein the low frequency transducer is capable of vibrating debris to allow sanitizing radiation to impinge under at least a portion of the debris.

In a sixth embodiment, a sanitizing apparatus of each of the above embodiments is provided further having a shutter mechanism whereby the shutter mechanism is capable of opening and closing when a sensor switch is activated and deactivated.

In a seventh embodiment, a sanitizing apparatus of each of the above embodiments is provided wherein the sensor switch is chosen from a pressure switch, a light switch, a contact switch, a toggle switch, an electrical switch, and a mercury tilt switch.

In an eighth embodiment, a sanitizing apparatus of each of the above embodiments is provided wherein instead of a structural layer positioned covering the top of the cells, individual glass plugs positioned into the top of each cell, wherein the glass plug allows at least a portion of the sanitizing radiation to pass through.

DETAILED DESCRIPTION OF THE DISCLOSURE

As used herein the term UVC refers to electromagnetic radiation with wavelengths ranging between 100-280 nanometers, inclusively.

As used herein the term UVC refers to electromagnetic radiation with wavelengths ranging between 280-315 nanometers, inclusively.

A sanitizing apparatus is provided for the elimination or significant reduction of undesirable or pathogenic microorganisms from objects, containing a housing having a top, a bottom and sides, wherein the volume of the housing is segmented into an array of individual, interconnected, geometrically shaped cells, each cell having sides that define the cell. The sides of the cells are made of structural material and are positioned orthogonal to the bottom of the housing and extend from the bottom of the housing fully or partially to the top of the housing, each cell having at least one of a sanitizing radiation emitter, an infrared radiation sensor, and a visible radiation sensor, positioned in the area of the bottom of the cell.

Figure 1:
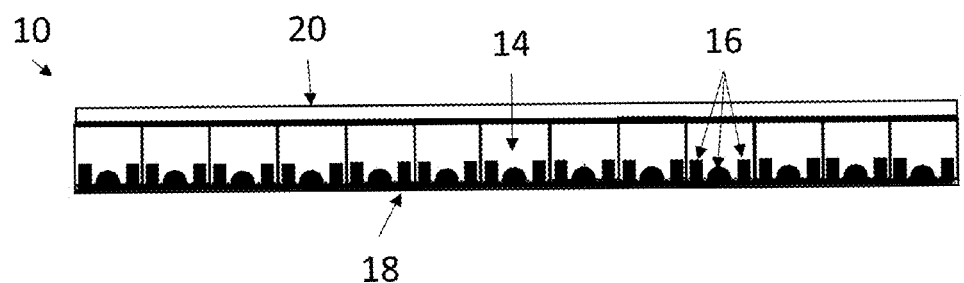
FIG. 1 shows a graphic representation of a side view of an exemplary embodiment of the sanitizing apparatus of current disclosure designed to eliminate or significant reduce undesirable or pathogenic microorganisms from objects with sides removed so that the inner structures can be seen and explained.

FIG. 1 shows a graphic representation of a side view of an exemplary embodiment of the sanitizing apparatus of current disclosure designed to eliminate or significant reduce undesirable or pathogenic microorganisms from objects containing a housing 10, with sides removed so that the inner structures can be seen and explained, a bottom 18 and a top 20. A grid of geometrically shaped cells 14 is positioned within the volume of the housing 10, and running from the bottom to fully or partially to the top. Positioned at the bottom of each cell 14 are at least one component chosen from a sanitizing radiation emitter, an infrared radiation sensor, and a visible radiation sensor 16.

The housing 10, including the bottom, the sidewalls and the geometrically shaped cells 14 may be made from any of a number of structural materials well known in the art including, for example, plastic, metal, wood and other structural material. The walls of the cells 14 may be made from material which is reflective to UV sanitization radiation, for example UVB and/or UVC radiation, such as, for example, aluminum. Alternatively, the walls of the cells may have a coating or other surface treatment that allows reflection of UV sanitization radiation, for example UVB and/or UVC radiation, such as, for example, aluminum. The reflective surfaces may help to direct stray sanitizing radiation to the top of the housing and onto surfaces to be sanitized thus providing increased radiation intensity. The cell walls could be vertical or could be slanted in or out depending on the desired design of the device and the design for collecting stray light and reflecting it upward toward the object to be sanitized.

The top of the device 20 comprises a structural layer covering the tops of all the individual cells contained in the housing and may be made from any structural material which can hold weight up to about 400 pounds and also allow at least a portion of the sanitizing UVC and/or UVB radiation, to pass through to the object being sanitized, such as, for example, plexiglass, quartz glass, polythene and the like. Although not shown, the devices may be fitted with shock absorbing materials positioned between the top and areas where the top comes into contact with the housing and/or the cell walls. Usefully materials for shock absorbing are well known in the art and include, for example, silicone pads, rubber inserts and the like.

Figure 2:
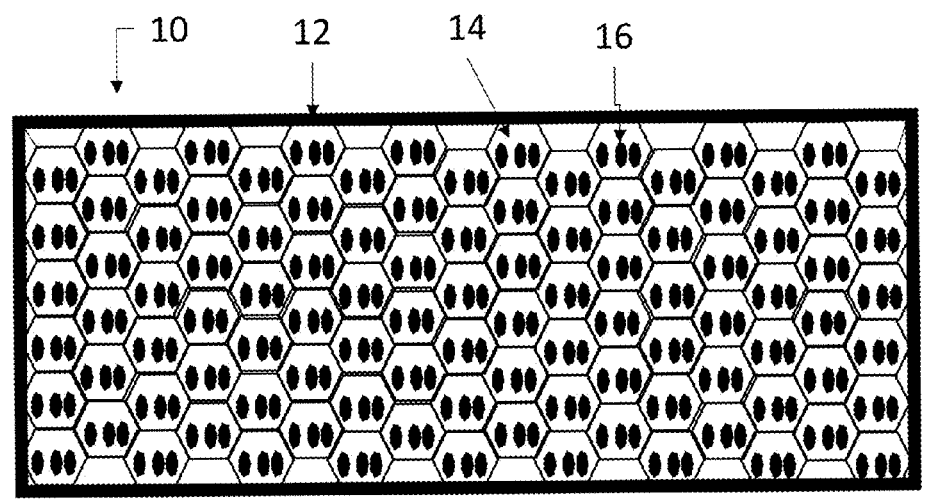
FIG. 2 shows a graphic representation of a top view of an exemplary embodiment of the sanitizing apparatus of current disclosure showing a honeycomb configuration of the array of cells.

FIG. 2 shows a graphic representation of a top view of an exemplary embodiment of the sanitizing apparatus of current disclosure 10 designed to eliminate or significant reduce undesirable or pathogenic microorganisms from objects showing a honeycomb configuration of the array of cells 14 that fill the volume of the housing 12. Also shown, positioned at the bottom of each cell 14 are at least one of a sanitizing radiation emitter, an infrared radiation sensor, and a visible radiation sensor 16.

Figure 3:
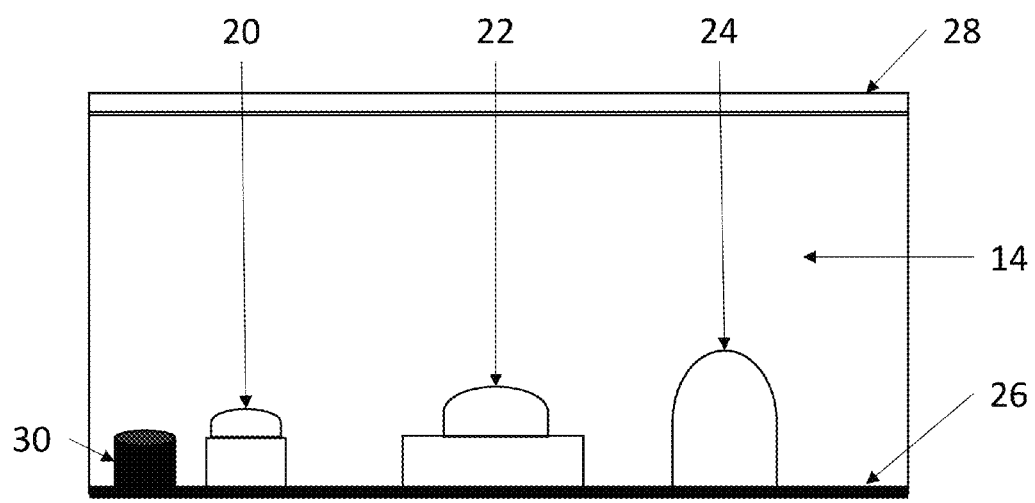
FIG. 3 shows a graphic representation a single cell 14 positioned within the housing of the current disclosure.

FIG. 3 shows a graphic representation a single cell 14 positioned within the housing of the current disclosure. The cell contains a UV LED radiation emitter 22, a visible/IR light sensor 20, and a blue LED emitter 24. Also graphically represented is a circuit board 26 which electronically interconnects the components, and microprocessor/logic 30 which controls the actions of the device.

The one or more UV LED radiation emitters 22 can predominantly emit a wavelength of 254-265 nm.

The most effective wavelength for killing or inactivating microorganisms is the 100-290-nm range, which is the UVC wavelength band. It is composed of short wavelengths from 200 to 280 nm. Currently commercially available LED lamps that give off wavelengths in the UVC spectrum, which is near the optimum for killing or inactivating microorganisms are useful for the present disclosure. Low-pressure mercury-vapor lamps can also be used in the present disclosure but are less desirable because they are larger than LED devices. UVC and UVB LED emitters contain silicon lenses which offers protection, long life and structural stability.

Not to be held to theory, a wavelength of UVC and or UVB radiation will break down the molecular bonds within the DNA of micro-organisms producing thymine dimers in their DNA thereby destroying them, rendering them harmless or prohibiting growth and reproduction. It is a process similar to the UV effect of longer wavelengths UVB on humans.

Figure 4:
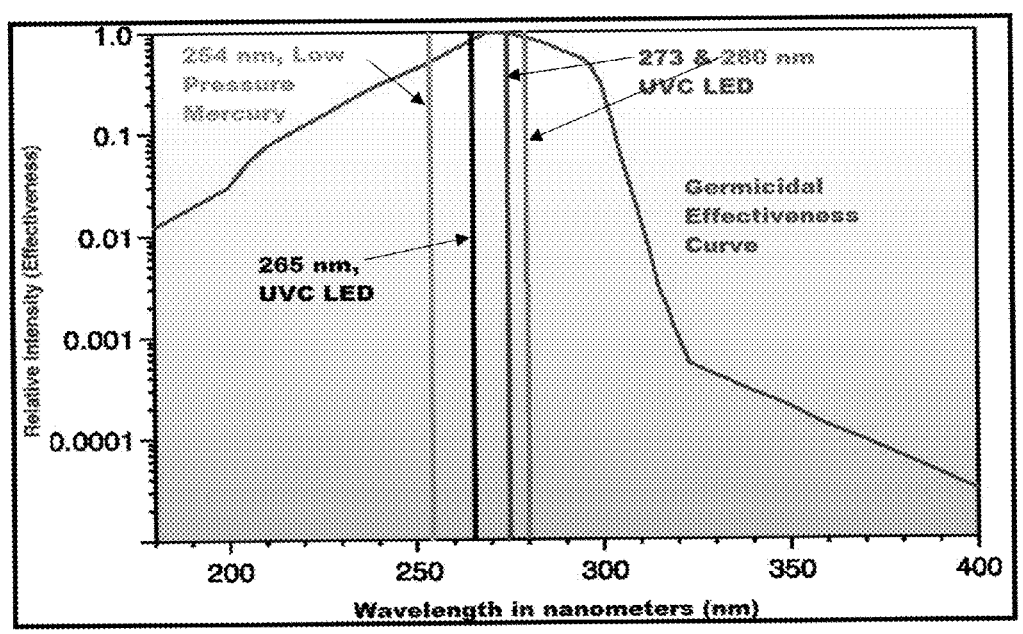
FIG. 4 shows the Germicidal Effectiveness Curve as well as the peak outputs of UVC and UVB LED radiation emitters compared to relative intensity

FIG. 4 show the Germicidal Effectiveness Curve as well as the peak outputs of UVC and UVB LED radiation emitters compared to relative intensity. As can be seen the LEDs emit quite readily in the germicidal areas. As can also be surmised, the device of the current disclosure can contain more than one LED which can emit in other specific areas of the UV spectrum to cover more wavelengths. The choice of LED emitters may be driven by what pathogen is desired to receive maximum exposure to sterilizing radiation.

As an example, commercially available UVC LED germicidal lamps range in input power from about 220 to 500 $\mu W/cm^2$ at a distance of 1 meter from the tube. Power intensity of approximately 1400 to 2800 $\mu W/cm^2$ measured at a distance of 1 inch from the LED surface is achievable.

Again not to be held to theory, it has been reported that to reach a 99% kill rate of *bacillus anthracis* a dosage of 8,700 $\mu W\ second/cm^2$ is required. Thus, in the current example and using the equation: Intensity×Exposure Time=$\mu W\ second/cm^2$, a lamp with a minimum power intensity of 1400 $\mu/cm^2$ at 1 inch from the bulb surface, an exposure time of less than 7 seconds is required. Of course a longer time will improve the kill rate for *bacillus anthracis*. Other notable 99% kill rate exposure requirements for UVC (measured in $\mu W/cm^2$) are: *E. coli*=6500, *Salmonella typhosa*=6000, Dysentery=4200 and Cholera=6500. It should be noted that in the example a 7 second exposure would be sufficient to provide a 99% kill rate of all the aforementioned bacteria. Viruses are also killed by UVC, some of the toughest being poliovirus and rotavirus, which require 21,000 $\mu W/cm^2$ for a 99% kill rate. Thus using the lamps of the above example, a 15 second exposure would provide a 99% kill rate. Also molds and yeasts can be killed by UVC exposure.

In one embodiment of the current disclosure the apparatus contains a visible and/or infrared radiation sensor which is electronically coupled to the UVC/UVB sanitizing radiation emitter. In operation, the visible/IR sensor registers ambient light such as visible and/or infrared light, and sends a signal to the microprocessor which sends a signal to the LED to remain off. When an object, such as, for example, a person's shoe covers the cell, the vis/IR sensor receives no vis/IR light and signals the microprocessor that no vis/IR is being sensed and the microprocessor will send a signal to the UVC/UVB LED to start emitting sanitizing radiation which then starts the sanitization process for the bottom of, in this example, the shoe. Thus, only when the cell is covered will UVC/UVB radiation be emitted from the LED emitter. When the object, such as a shoe, uncovers the individual cell, the vis/IR sensor will sense vis/IR radiation and send a signal to the microprocessor to shut off the UVC/UVB LED. This device and method prevents stray UVC/UVB radiation from escaping into the environment where it is undesirable.

The apparatuses are configured to run on readily available electric power from a wall socket or they may be hard-wired into an electric system either 110 or 220 volt or the like. In some embodiments the apparatuses are configured to be interconnected such that an array of apparatuses can fill a large space, such as, for example, the floor of a lobby, an airport terminal, the floor of a hospital, bathroom floors, hallways, or any large area where sanitization of the bottom of objects such as shoes, boots, etc. is desired. While interconnected each apparatus and cell works independently to activate and deactivate the sanitizing radiation. In practice some or all of the apparatuses may be interconnected. In the array embodiment, for example, a person can walk across the array as the soles of the shoes get sanitized. During a step, the sole dynamically covers and uncovers the individual cells. Thus portions or all of the sole are being sanitized at any one particular time while a person is walking across the array of sanitizing apparatuses.

In another embodiment of the current disclosure the apparatus further contains a low frequency transducer. The low frequency transducer is designed to send ultrasonic waves through the cell walls as well as through the air contained in each cell to vibrate particles and other debris so that the UVC/UVB radiation may expose areas under the debris in order to obtain a more complete sanitization. Since sanitizing radiation is a line of capable of vibrating debris to allow sanitizing radiation to impinge under at least a portion of the debris.

Figure 5:
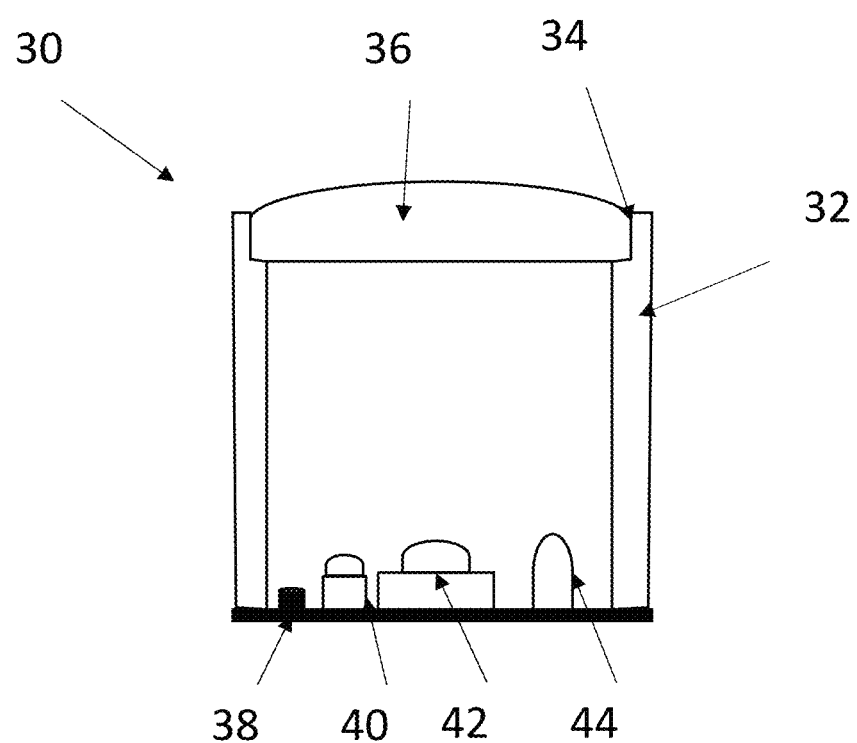
FIG. 5 shows an embodiment of the current disclosure wherein the top of each individual cell is covered with a plug made of structural material.

As mentioned the cells many be covered with a structural layer that cover the tops of all the cells contained in the housing. In another embodiment, and shown in FIG. 5 the top of each individual cell is covered with a plug made of structural material. As used here in the term plug means a piece of material which fits into the top of one cell. In FIG. 5 the plug 36 fits into the cell 30 and is supported by a recess 34 in the cell sidewall 32. Also shown are the microprocessor 38, the Vis/IR sensor 40, the UVC/UVB LED emitter 42 and a blue LED 44. The plug is made from the structure materials mentioned supra that allow at least a portion of the Vis/IR/UVC/UVB radiation to pass through. The thickness of the plug may be chosen to allow the top of the plug to be essentially level with the top of the cell sidewall. Of course other configurations may be used such as, for example, the plug may act as a lens having a convex surface for focusing the radiations, the plug may fit slightly higher or lower than the top of the cell walls for purposes, such as, for example, ease of cleaning.

Figure 6A:
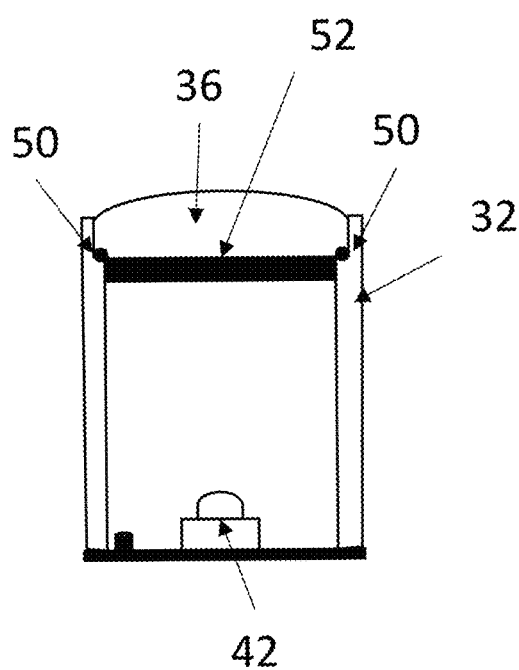
FIG. 6A shows a further embodiment of the current disclosure in which shutters are in a closed position.
Figure 6B:
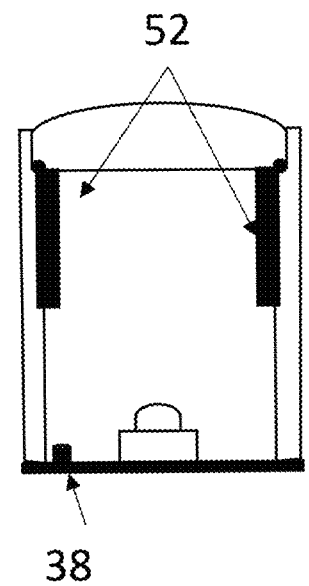
FIG. 6B shows a further embodiment of the current disclosure in which shutters are in an open position.

A further embodiment of the current disclosure includes a shutter mechanism which opens and closes to allow sanitizing radiation to pass through to the object being sanitized. As shown in FIG. 6A the cell contains sensors 50, in this case, pressure sensors beneath the plug which send a signal to the microprocessor 38 which then signals the shutters 52 to open and signals the UVC/UVB LED 42 to emit sanitizing radiation. FIG. 6B shows the shutter in an open position. The sensors may be, for example, pressure sensors, optical sensors, contact switches, toggle switches, electric switches, or tilt switches, which signal that something is positioned on the cell for sanitization. The shutter may be any of a number of materials well known in the art with mechanisms that will open the shutters and in some cases pivot around an axel, not shown. In other embodiments the shutters may include mechanisms such as, for example, "muscle wires" or piezoelectric mechanisms to open and close the shutters. A muscle wire is an extremely thin wire made of nickel-titanium alloy that contracts when an electric current is applied and releases back to its original position when the electric current is removed. In the current disclosure the muscle wire would receive an electric signal from the microprocessor to contract and release, opening and closing the shutters when the sensor under the plug is activated.

What is claimed is:

1. A sanitizing apparatus comprising:
a housing comprising a top, a bottom and sides,
wherein the volume of the housing is segmented into an array of individual, interconnected, cells, each cell having sides that define the cell,
wherein the sides of the cells comprise structural material and are positioned orthogonal to the bottom of the housing and extend from the bottom of the housing fully or partially to the top of the housing, each cell comprising, at least one of a sanitizing radiation emitter, an infrared radiation sensor, and a visible radiation sensor, positioned in the bottom of the cell.

2. The apparatus of claim 1, wherein the housing top comprises a structural layer positioned covering the tops of the cells, wherein the layer allows at least a portion of the sanitizing radiation to pass through.

3. The apparatus of claim 1, wherein the infrared radiation sensor is electronically coupled to the sanitizing radiation emitter, and wherein the sanitizing radiation emitter is capable of being activated when the infrared sensor senses no infrared radiation.

4. The apparatus of claim 1, further comprising electrical connectors wherein the electrical connectors are configured to allow at least two apparatuses to be electronically connected.

5. The apparatus of claim 1, further comprising a low frequency transducer, wherein the low frequency transducer is capable of vibrating debris to allow sanitizing radiation to impinge under at least a portion of the debris.

6. The apparatus of claim 1, wherein the sidewalls of the individual cells comprise a recess into which individual plugs may be positioned into the top of each cell, wherein the plug comprises a thickness that allows the top surface of the plug to be essentially level with the top to the unrecessed portion of the cell sidewall, and wherein the plug is comprised of material which allows at least a portion of the sanitizing radiation to pass through.

7. The apparatus of claim 6, wherein the infrared radiation sensor is electronically coupled to the sanitizing radiation emitter, and wherein the sanitizing radiation emitter is capable of being activated when the infrared sensor senses no infrared radiation.

8. The apparatus of claim 6, further comprising electrical connectors wherein the electrical connectors are configured to allow at least two apparatuses to be electronically connected.

9. The apparatus of claim 6, further comprising a low frequency transducer, wherein the low frequency transducer is capable of vibrating debris to allow sanitizing radiation to impinge under at least a portion of the debris.

10. The apparatus of claim 6, wherein each cell further comprises a shutter mechanism.

11. The apparatus of claim 10 further comprising a sensor switch coupled to the shutter mechanism whereby the shutter mechanism is capable of opening and closing when a sensor switch is activated and deactivated.

12. The apparatus of claim 11, wherein the sensor switch is chosen from a pressure switch, a light switch, a contact switch, a toggle switch, an electrical switch, and a mercury tilt switch.

13. The apparatus of claim 10, wherein the infrared radiation sensor is electronically coupled to the sanitizing radiation emitted, and wherein the radiation emitter is capable of being activated when the infrared sensor senses no infrared radiation.

14. The apparatus of claim 10, further comprising electronic connectors wherein the electronic connectors are configured to allow at least two apparatuses to be electronically connected.

15. The apparatus of claim 10, further comprising a low frequency transducer, wherein the low frequency transducer is capable of vibrating debris to allow sanitizing radiation to impinge under at least a portion of the debris.

* * * * *